United States Patent [19]

Arima et al.

[11] 4,257,868

[45] Mar. 24, 1981

[54] AUTOMATIC SERUM APPLICATOR WITH SERUM DRYING-PREVENTIVE MECHANISM

[75] Inventors: Heihachi Arima, Hachiouji; Toshio Shinohara, Chofu, both of Japan

[73] Assignee: Olympus Optical Co., Ltd., Tokyo, Japan

[21] Appl. No.: 134,333

[22] Filed: Mar. 26, 1980

[30] Foreign Application Priority Data

Mar. 30, 1979 [JP] Japan .................. 54-37974

[51] Int. Cl.³ .................. G01N 27/26; G01N 27/28
[52] U.S. Cl. .................. 204/299 R; 204/180 G; 204/180 S
[58] Field of Search ........... 204/180 G, 180 S, 299 R; 424/12; 23/230 B

[56] References Cited

U.S. PATENT DOCUMENTS

| | | | |
|---|---|---|---|
| 3,317,418 | 5/1967 | Zec | 204/299 R |
| 3,421,998 | 1/1969 | Yallen | 204/299 R |
| 3,428,547 | 2/1969 | Zec | 204/299 R |
| 3,616,387 | 10/1971 | Siebert et al. | 204/299 R X |
| 3,839,183 | 10/1974 | Klein et al. | 204/299 R |
| 4,199,428 | 4/1980 | Hayashi et al. | 204/299 R |

*Primary Examiner*—Arthur C. Prescott
*Attorney, Agent, or Firm*—Cushman, Darby & Cushman

[57] ABSTRACT

In an automatic serum applicator so adapted as to insert blade tips of a serum applicating member into sera filled in sample trays for applying sera to said blade tips and place said blade tips onto carrier to apply said sera, an automatic applicator with serum drying-preventive mechanism adapted in such a manner that a water-absorptive sheet impregnated with water is placed in a case for accommodating sample trays, a lid covering said case is arranged in a freely openable-closable condition and said lid is opened only when the serum is to be applied to the applicating member, thereby preventing sera contained in sample trays from being dried.

4 Claims, 3 Drawing Figures

AUTOMATIC SERUM APPLICATOR WITH SERUM DRYING-PREVENTIVE MECHANISM

BACKGROUND OF THE INVENTION (a) Field of the Invention

The present invention relates to an automatic serum applicator to be used for a electrophoresis, and more specifically to an automatic applicator equipped with serum drying-preventive mechanism.

(b) Description of the Prior Art

There have already known certain types of apparatuses which have automated steps of electrophoresis such as application of serum onto carrier and formation of fractionated patterns by electrical energizing. Among these apparatuses, an automatic serum applicator uses an applicating member having a large number of applying blades and applies samples, for example sera, onto carriers by inserting the blade tips into sample trays filled with sera for adhering them to the blade tips and then lowering the applicating member onto the carriers. After application of the sera, the automatic serum applicator shifts the applicating member into a washing bath to wash off the sera remaining on the blade tips with washing water and, after washing, removes the washing water from the blade tips by a means such as drying or absorbing into filter paper, etc. At the subsequent stages, the automatic serum applicator repeats the above-mentioned steps for applying other sera repeatedly.

The automatic serum applicator described above has a defect that it allows sera to be dried while being kept in the sample trays arranged in the serum applicator, thereby giving adverse effect on inspection results. The above-mentioned defect is very serious especially when a large number of sample trays are arranged in the automatic serum applicator and sera filled in these sample trays are consecutively applied onto carriers by repeating the above-described steps.

In order to correct the above-mentioned defect, it was conventionally practiced to blow temporarily moistened air into the automatic serum applicator to prevent sera from being dried for enhancing humidity in the automatic serum applicator. However, it was impossible to obtain sufficient drying-preventive effect due to influence from air outside the automatic serum applicator, and especially to keep sample trays in set condition for a long time for treating a large number of sera.

SUMMARY OF THE INVENTION

A general object of the present invention is to provide an automatic applicator with serum drying-preventive mechanism adapted in such a manner that a water-absorptive sheet impregnated with water is placed at the location to set the sample trays, the location is covered with a lid and the lid is automatically opened only when sera are to be applied to the blade tips of the serum applicating member.

DETAILED DESCRIPTION OF PREFERRED EMBODIMENT

Figure 1:
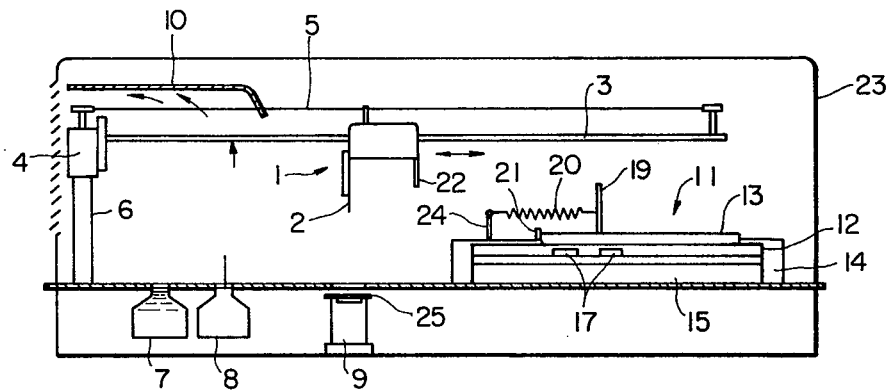
FIG. 1 shows a diagram illustrating the construction of the automatic applicator with serum drying-preventive mechanism according to the present invention.
Figure 2:
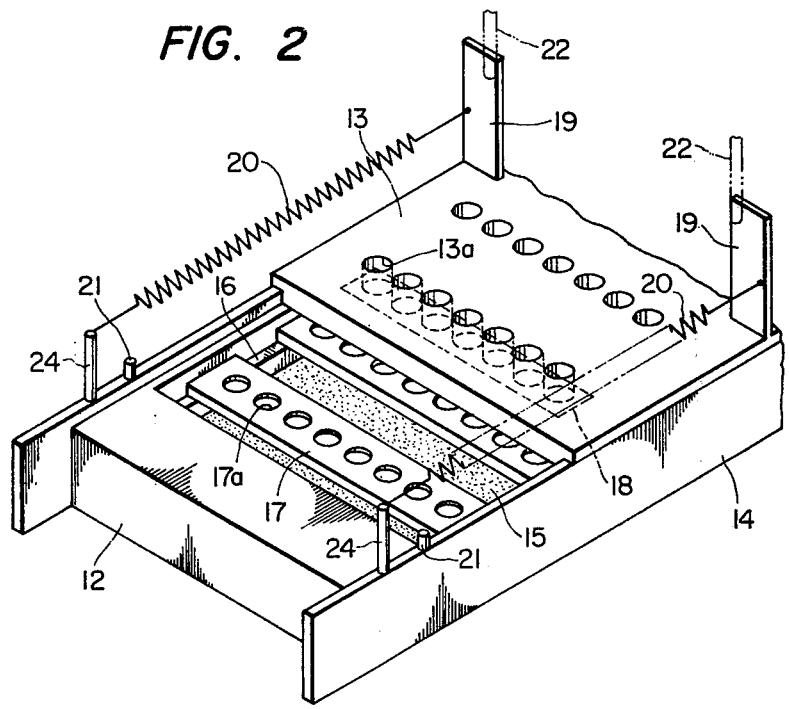
FIG. 2 shows a perspective view illustrating portion of the serum drying-preventive mechanism arranged in the automatic applicator according to the present invention.
Figure 3:
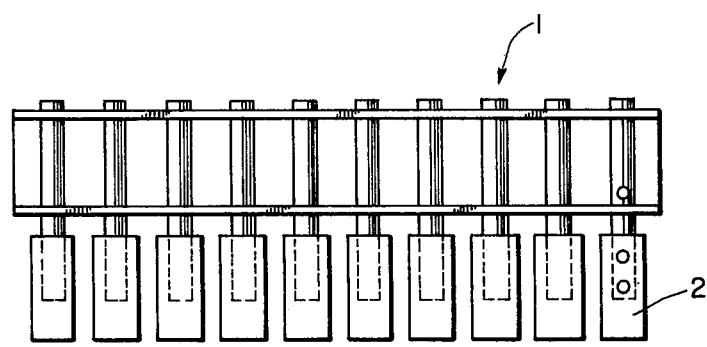
FIG. 3 shows a front elevation illustrating an example of the serum applicating member used in the automatic serum applicator according to the present invention.

Now, the serum applicator according to the present invention will be described with reference to an embodiment shown in the accompanying drawings. In FIG. 1, the reference numeral 1 represents a serum applicating member which supports a large number of blades arranged as illustrated in FIG. 3 (in FIG. 1, said blades are arranged in the direction perpendicular to the paper surface). The reference numeral 3 designates a guide rod to which the serum applicating member 1 is supported so as to be shiftable along this guide rod. The reference numeral 4 denotes an applicating member driving mechanism which functions to move a wire 5 to shift the serum applicating member 1 fixed to said wire 5, and vertically move up and down the serum applicating member 1, guide rod 3, wire 5, etc. all together along a support 6. The reference numeral 7 represents a washing water bath for washing the blade tips, the reference numeral 8 designates a blade tip drying bath, the reference numeral 9 denote a carrier stand and the reference numeral 10 represents a duct which is arranged for preventing sera from being dried by air from the drying bath. The reference numeral 11 designates a serum drying-preventive mechanism which consists of a case 12 and a lid 13 arranged shiftably along a guide 14. The case 12 has such a construction as shown in FIG. 2 and contains a water-absorptive sheet 15 impregnated with water. Attached to both the inside surfaces of the case 12 is a support flame 16 which mounts sample trays having plural number of concavities filled with sera. Formed in the lid 13 are a large number of openings 13a arranged in rows at the sera to be located over the sample trays 17 when the lid is placed in the closed condition. These openings are formed at definite intervals in plural rows. To the lower surface of the lid 13, a water absorptive sheet impregnated with water is bonded at a location corresponding to the raws of the openings 13. The reference numeral 19 represents a lid-shifting plate attated to the lid 13, and the reference numeral 20 designates a spring which is stretched between a pin 24 arranged on the guide plate 14 and the lid-shifting plate 19, said spring always pulling the lid 13 in the closing direction. The reference numeral 21 denotes a stopper. The reference numeral 22 represents a lid-shifting pin which is attached to the serum applicating member and functions to push the lid-shifting plate 19 for opening the lid 13 against force of the spring 20 when the serum applicating member is shifted rightward from the position shown in FIG. 1. The reference numeral 23 designates a cover for protecting the entire serum applicator.

Now, operation of the automatic serum applicator having the above-described construction will be explained. First, a carrier 25 to be applied with sera is fed into the serum applicator in the direction perpendicular to the paper surface of FIG. 1 by a suitable conveying mechanism and placed on the stand 9. Then, the driving mechanism 4 is a actuated to move the wire 5 for shifting the serum applicating member 1 rightward. Since the lid-shifting pin 22 is moved together with the serum applicating member and pushes the lid-shifting plate 19 arranged on the lid 13, it is shifted rightward in FIG. 1 and opened. The serum applicating member stops when the lid is opened and blade tips 2 of the serum applicating member are located just over the sample trays 17. In this condition, the lid 13 is so adapted as to be open only at the areas over the sample trays 17 as shown in FIG. 2. At this position, the driving mechanism 4 operates to lower the guide rod 3 so that the serum applicating member 1 is lowered until the blade tips 2 are dipped into sera in the sample trays and soaked with sera, and then hoist up the guide rod and the serum applicating member. Successively, the serum applicating member is shifted leftward in FIG. 1 and then stopped at the position to apply the sera to the carrier 25. In this condition, the serum applicating member is set in the position shown in FIG. 1 and the spring is shifted leftward under the force of the spring to close the case. At this position, the serum applicating member 1 is lowered down to apply the sera to the carrier 25. Further, the blade tips of the serum applicating member are dipped and washed in washing water in the water washing bath 7 by the vertical and horizontal motions of the serum applicating member similar to those described above. After the washing, the blade tips are placed and dried in the drying bath 8 to complete a single cycle. By the way, the method to moisten air in the case is not limited to arranging a water-absorptive sheet impregnated with water. Further, it will be possible to arrange a single sample tray only or plural sample trays at definite intervals and shift them consecutively leftward for a distance corresponding to that between two neighboring sample trays at each cycle by using an adequate conveying mechanism. Though the above-described embodiment is so adapted as to remove the washing water from the blade tips after washing by using the drying bath 8, it will be possible to adopt a method using filter paper for wiping the blade tips. Similarly, the components other than the serum drying-preventive mechanism may have constructions which are different from those used in the above-described embodiment. As is clear from the foregoing descriptions, the automatic serum applicator according to the present invention maintains sample trays in a case which is enclosed at the steps other than that for applying sera to the blade tips and adequately moistened with a water-absorptive sheet impregnated with water, and therefore permits measurements in favorable condition while preventing sera from being dried.

We claim:

1. In an automatic serum applicator so adapted as to insert the blade tips of a serum applicating member into sera filled in sample trays for applying sera to said blade tips and then place said blade tips onto a carrier for serum application, an automatic applicator with serum drying-preventive mechanism comprising a case for accommodating said sample trays, a member placed in said case for moistening air in said case and a lid for covering said case, said automatic applicator being adapted in such a manner that said case is opened and closed in conjunction with operations of said serum applicating member and said lid is opened only when sera are to be applied to a carrier by operating said serum applicating member.

2. An automatic applicator with serum drying-preventive mechanism according to claim 1 wherein said member for moistening air in said case is a water-absorptive sheet impregnated with water.

3. An automatic applicator with serum drying-preventive mechanism according to claim 2 wherein another water-absorptive sheet impregnated with water is bonded to the rear surface of said lid.

4. An automatic applicator with serum drying-preventive mechanism according to claim 1 further comprising a lid shifting plate arranged on said lid and a lid shifting pin arranged on said serum applicating member, whereby shift of said lid shifting pin along with shift of said serum applicating member causes said lid shifting pin to move said lid shifting plate so as to open said lid.

* * * * *